US010556652B2

(12) United States Patent
Penari et al.

(10) Patent No.: US 10,556,652 B2
(45) Date of Patent: Feb. 11, 2020

(54) VESSELS COMPRISING A COMPOSITE ENVELOPE

(71) Applicant: Metalskin Technologies SAS, Balaruc-Bains (FR)

(72) Inventors: Stephane Penari, Balaruc-les-Bains (FR); Thomas Drean, Balaruc-les-Bains (FR); Yann Dube, Balaruc-les-Bains (FR)

(73) Assignee: Metalskin Technologies SAS, Balaruc-Bains (FR)

( * ) Notice: Subject to any disclaimer, the term of this patent is extended or adjusted under 35 U.S.C. 154(b) by 239 days.

(21) Appl. No.: 15/544,653

(22) PCT Filed: Jan. 19, 2016

(86) PCT No.: PCT/EP2016/051017
§ 371 (c)(1),
(2) Date: Jul. 19, 2017

(87) PCT Pub. No.: WO2016/116446
PCT Pub. Date: Jul. 28, 2016

(65) Prior Publication Data
US 2017/0361907 A1 Dec. 21, 2017

(30) Foreign Application Priority Data
Jan. 19, 2015 (FR) .................................... 15 50407

(51) Int. Cl.
B32B 3/00 (2006.01)
B63B 59/04 (2006.01)
(Continued)

(52) U.S. Cl.
CPC .............. B63B 59/04 (2013.01); A01N 25/08 (2013.01); A01N 59/26 (2013.01); B29C 70/28 (2013.01);
(Continued)

(58) Field of Classification Search
CPC ...... C09D 5/1618; C09D 5/1662; C09D 7/61; B63B 59/04
See application file for complete search history.

(56) References Cited

U.S. PATENT DOCUMENTS

| 5,571,312 A | 11/1996 | Andoe | |
|---|---|---|---|
| 5,814,172 A * | 9/1998 | Cox | B63B 59/04 114/222 |
| 7,842,288 B2 * | 11/2010 | Weed | B05D 7/54 106/1.23 |

FOREIGN PATENT DOCUMENTS

| DE | 19645554 A1 | 5/1998 |
|---|---|---|
| EP | 0510850 A1 | 10/1992 |

(Continued)

OTHER PUBLICATIONS

Motor Boat Magazine, No. 282 Jun. 2013, pp. 133-137.
(Continued)

Primary Examiner — Elizabeth E Mulvaney
(74) Attorney, Agent, or Firm — Banner & Witcoff, Ltd.

(57) ABSTRACT

The invention relates to a hull of a vessel having characteristic surface properties, allowing an increase in surface runoff while benefiting from an inherent anti-fouling property and an original aesthetic appearance. Furthermore, the invention allows the incorporation of said outer composite envelope into the structure of the hull, thereby preventing delamination problems and inherently providing a vessel hull with the above-mentioned properties.

20 Claims, 1 Drawing Sheet

(51) Int. Cl.
    *C09D 7/61*         (2018.01)
    *C09D 5/16*         (2006.01)
    *A01N 25/08*       (2006.01)
    *A01N 59/26*       (2006.01)
    *B29C 70/28*       (2006.01)
    *B29C 70/58*       (2006.01)
    *C08K 3/015*       (2018.01)
    *B29K 67/00*       (2006.01)
    *B29K 505/10*      (2006.01)
    *B29L 31/30*       (2006.01)

(52) U.S. Cl.
    CPC ............ *B29C 70/58* (2013.01); *C09D 5/1618* (2013.01); *C09D 5/1662* (2013.01); *C09D 7/61* (2018.01); *B29K 2067/00* (2013.01); *B29K 2505/10* (2013.01); *B29L 2031/307* (2013.01); *C08K 3/015* (2018.01)

(56) References Cited

FOREIGN PATENT DOCUMENTS

WO     2005/056699 A1     6/2005
WO     2014/055418 A1     4/2014

OTHER PUBLICATIONS

Database CA [Online] Chemical Abstracts Service, Columbus, Ohio, US; Dec. 9, 2008 (Dec. 9, 2008).
Singh, N. et al., Leaching of copper and zinc from spent antifouling paint particles, Environmental Pollution, 2009, vol. 157, No. 2, pp. 371-376.

* cited by examiner

VESSELS COMPRISING A COMPOSITE ENVELOPE

RELATED APPLICATIONS

This application is a National Stage Application under 35 U.S.C. 371 of co-pending PCT application PCT/EP2016/051017 designating the United States and filed Jan. 19, 2016; which claims the benefit of FR application number 1550407 and filed Jan. 19, 2015 each of which are hereby incorporated by reference in their entireties.

The object of the present invention relates to a vessel hull, as well as to the vessel as such, comprising an outer envelope having a variety of technical effects related to the fact that said envelope comprises a particular metal powder. Further, the present invention relates to a method for manufacturing such a vessel hull, as well as to the vessel hull which may be obtained by this method.

INTRODUCTION

At the beginning of the 80s, a novel technique appeared and revolutionized the way how the world works the metal.

This technique (a so called cold metallization technique) schematically consists of associating metal and a binder, giving the possibility of rapidly covering nearly any support, regardless of the shape or of the nature (laminates, melamine laminates, wood, plastics, plaster, glass fiber, ceramic, concrete, foams, china, glass and metal), by fitting all the details thereof. These composites, formed with micronized metal granulates, of a hybrid polymeric binder and of a catalyst, produce very strong adhesion between the composite and the support. The catalyzed composite metals may further be sanded, sand blasted, polished, brushed, acidified, oxidized, etched (if the thickness allows this), varnished and treated exactly in the same way as massive metal for a fraction of the cost. Further, the composite layer does not conduct electricity and does not corrode the support, which distinguishes it from metal.

This composite is applied both to "red" and "gray" metals and alloys and is regularly enriched with novel metals/alloys.

Thus, the technology of cold metallization is commonly accomplished by means of a standard gun-painting equipment. The composite metals are cold sprayed by means of an HVLP (high volume/low pressure) gun with adapted nozzles. This method gives the possibility of applying a thin layer of composite on the support. There is no limitation as to the thickness, except that one must proceed with several applications resulting in a multilayer. The good economical compromise up till now was however around 0.015 to 0.07 mm of thickness, which may be obtained in a single layer.

Recently, the Applicant showed that copper composites are very well adapted for coatings of the "anti-fouling" type in the nautical field (cf. for example the article published in "Motor Boat Magazine", no. 282 June 2013, pages 133-137).

The products developed by the Applicant further gave the possibility of reducing the consumption and/or a gain in speed of the relevant vessel. No explanation up till now gave the possibility of justifying this effect: Was this due to the spraying mode, to the chemical nature of the metal of the composite, to the chemical nature of the binder, or further to a particular shape of the powder grains?

It was reported in FR1357099 that a particular grain size had to be observed so that the copper powder (oxidized/phosphorus-containing) may be incorporated into the binder.

Now, a reduction in the consumption and/or a gain in speed of the relevant vessel was also ascertained on these composites. Several other metal powders were tested with the same grain size and the effect was again found. Thus, and this in the origin of the present invention, it would seem that it is the particular grain size of the tested powder which is at the origin of this effect and this independently of the chemical nature of the metal powder. Thus a powder of copper, aluminium or of another metal for example.

Further, the vessels remaining in the liquid medium for long periods of time, the daily wear related to this particular use makes standard metallization techniques less attractive than the method for manufacturing a vessel hull according to the present invention which may generate a larger outer layer thickness and avoids delamination of the coating. Thus, another aspect of the present invention relates to a method for manufacturing a vessel hull, such as a boat, which allows longer lifetime of the outer layer loaded with metal/composite powder. This method moreover allows, if this is desired, the creation of a concentration gradient of powder grains in the outer layer. Further, the obtaining method according to the present invention gives the possibility of retaining the properties inherent to metal powders (such as the biocidal or anti-fouling property).

Finally, in a quite surprising way, the thickness generates the outer layer of the vessel hull comprising the metal powders gives an unprecedented esthetical aspect of vessels made with this method. This aspect is both related to the particular grain size of the powder used, to the thickness of the layer, to the possibility of generating a concentration gradient, to the outer liquid environment and to the possibility of varying the chemical nature of the powder grains in order to obtain more or less colored, coppery, silvery, dull, tints, etc.

SUMMARY OF THE INVENTION

The object of the present invention relates to a vessel hull comprising in an external envelope intended to be in contact with an outer liquid element, a metal powder characterized in that:
said powder:
contains more than 30% by mass of grains for which the diameter is greater than 45 μm and
is partly in contact with said outer liquid element;
the external envelope has a thickness of less than 0.2 mm, advantageously less than 0.3 mm, 0.5 mm, 0.6 mm, 0.7 mm, 0.8 mm, 0.9 mm or 1 mm;
and that the powder comprises a copper powder with at least 60% by mass of copper based on the mass of powder.

In a particular embodiment, said external envelope comprises a concentration gradient of powder grains.

The powder grain gradient within the solidified binder matrix may be evaluated by scanning electron microscopy techniques and one skilled in the art has available in the technical literature different techniques for analysis and characterization of the microstructure of a material allowing him/her to show a gradient of metal powder particles. The analysis techniques by electron microscopy allow magnetications of the order of 5 to 60,000 times and the viewing as well as the distribution of particles of the size from a few microns to a few tens of microns are made possible. For example, the structural analyses such as described by the Centre de Transfert de Technologies Céramiques (CTTC, France) are adapted for such measurements.

The present invention also relates to objects which may be added to a vessel hull either comprising or not an outer envelope as described presently.

The object of the present invention therefore also relates to a hull, a foil, a directional element such as a rudder or a fin, a propulsion element such as a propeller or a jet pipe comprising an external envelope as defined presently.

The object of the present invention relates to a vessel comprising an external envelope as described presently, in particular at any of the following objects: at the vessel hull (in particular at the wet surface during navigation), at the hull, at a foil, at a directional element such as a rudder or a fin, or at a propulsion element such as a propeller or a jet pipe.

The object of the present invention also relates to a method for manufacturing a vessel hull as described presently comprising the following steps:

a. providing a binder/metal powder mixture,
 b. depositing a layer of the mixture on a mold of a vessel hull;
 c. optionally adding fiber materials in said binder;
 d. hardening the binder/metal powder mixture for example by treatment with light, with heat or by adding a hardening agent optionally added to the mixture;
 e. optionally adding at least one additional structure layer and/or reinforcement layer on the first hardened layer in step c.;
 f. removing the vessel hull from the mold;
characterized in that the metal powder contains more than 30% by mass of grains for which the diameter is greater than 45 µm.

According to a particular embodiment, the deposit of the layer of the mixture is achieved by spraying.

In another embodiment, the invention also relates to a method for manufacturing a vessel hull as described comprising the following steps:

a. providing a binder/metal powder mixture,
 b. depositing a layer of the mixture on the external face of a hull of a vessel,
 c. hardening the binder/metal powder mixture for example by treatment with light, with heat or by adding a hardening agent optionally added to the mixture,
 d. optionally adding at least one additional structure layer and/or reinforcement layer on the first hardened layer in step c,
characterized in that the metal powder contains more than 30% by mass of grains for which the diameter is greater than 45 µm.

The object of the present invention further relates to a vessel hull which may be obtained by the method as described presently.

DEFINITIONS

Vessel

The vessel according to the present invention is a boat, a sub-marine, a wind surfing board, a kite surf, a wake board, a surf, a paddle board, a jet ski, a canoe, a kayak, etc. Indeed, the external envelope according to the present invention gives the possibility of limiting the friction phenomena related to fluids which makes it also applicable to different sliding sport supports. Further, the vessel may be occupied by persons or remotely controlled.

Boat

The present invention may be applied to any boat such as sailing boats or with an engine, multi-hulls, hydrofoil boats, speed boats, ferries, tankers, inflatable boats, two container ships, freight ships, or further fishing boats such as trawlers.

Hull Shape

By "hull shape", is understood in the present invention the immersed portion of the hull of a ship, or of any other vessel, or the portion of the substrate (such as water skis for example) directly in contact with the outer liquid element causing friction.

Outer Liquid

By "liquid" meant according to the present invention any substance which continuously deforms under a shear stress which is applied to it. Thus, by outer liquid, is meant any liquid in which the vessel is able to move and/or float. Preferentially within the scope of the present invention, the outer liquid comprises water such as the sea, a lake, a river, a stream, a pond . . . .

Grain Size

The grain size is generally the study of the statistical distribution of the sizes of a plurality of units (or pieces/granules) which are naturally or in a fractionated way solid (i.e. a collection). The grain size analysis is the whole of the operations giving the possibility of determining the distribution of the sizes of the elements making up a powder. The grain size distribution is the representation in the form of tables of numbers or graphs of the experimental results of the grain size analysis. The grain size may be measured by any adequate way known to one skilled in the art and more particularly via the standardized method as described in the ISO4497 standard.

Powder

Generally, the powder is a fractionated state of the material. Thus this is a plurality of solid material units (or pieces/granules) with a size generally less than one tenth of a millimeter (100 µm) which form together a "collection". A powder is characterized in terms of physical properties by its grain size.

Oxidized Copper Powder

By "oxidized copper powder", it is understood according to the present invention on the one hand that the powder has the presently defined grain size characteristics (allowing its incorporation in a binder) and on the other hand that the powder has a content of oxidized copper greater than or equal to 5% by mass based on the total mass of copper in the powder preferentially greater than or equal to 10%, 20%, 30%, 40%, 50%, 60%, 70%, 80%, 90%, 95%, 99% or 100% by mass based on the total mass of copper in the powder.

Phosphorus-containing Copper Powder

By "phosphorus-containing copper powder", is understood according to the present invention on the one hand that the powder has grain size characteristics defined presently (allowing its incorporation into a binder) and on the other hand that the powder has a phosphorus content comprised between 2 and 16% by mass, preferentially 8%. Preferably, the phosphorus-containing copper powder consists in an alloy of copper and of phosphorus, preferentially $CuP_8$, preferentially at a copper-phosphorus content in percentage by mas equal to or greater than 84:16%, 85:15%, 86:14%, 87:13%, 88:12%, 89:11%, 90:10%, 91:9%, 92:8%, 93:7%, 94:6%, 95:5%, 96:4%, 97:3%, 98:2%, 99:1%, more preferentially greater than or equal to 92:8%. Preferably, the powder comprising copper-phosphorus comprises as a majority element in its composition of $CuP_8$, or consists in $CuP_8$, which may for example be comprised at a content equal to or greater than 50%, 60%, 70%, 80%, 90%, 95%, 99% of the total mass of the powder.

Core Oxidation

By "core oxidation", is meant according to the present invention that the grains of the powder of oxidized copper are both oxidized at the surface and in the centre of the grains which make up said powder. The oxidation level may nevertheless vary according to a straight line which would run from the surface of the grain at the centre (i.e. the centre of gravity) of the grain. Typically the surface of the grain is more oxidized than is the centre because of the greater entropy than has the surface. Advantageously, the centre has an oxidation level which is 50% by mass less than that of the surface, further more advantageously the centre has an oxidation level which is 25% by mass less than that of the surface, even more advantageously the centre has an oxidation level which is 10% by mass less than that of the surface, more advantageously than that, the centre has an oxidation level which is 5% by mass less than that of the surface, more advantageously the centre has an oxidation level which is identical to that of the surface.

Oxidation Level

Generally, the oxidation implies a loss of electrons from the oxidized entity. In the present invention, this is expressed by the reaction of oxygen with the metal in the powder, preferentially the copper. For example in the case when the powder initially only contains copper, the "oxidation level" according to the present invention then makes reference to the initial mass amount of copper in the oxidation state zero ("Cu$^0$") which is oxidized into CuO, i.e. the copper is in the oxidation state of +2. Generally, the oxidation level therefore makes reference to the amount of copper which is oxidized and therefore represents a ratio of quantities (mass, mole) of the copper which is engaged into the oxidation reaction.

Generally according to the present invention, as the amount of copper is preponderant, by measure of practicality, reference is made by approximation to mass levels. Strictly speaking, this would be molar levels. The conversion from mass content to molar contents is naturally within the reach of one skilled in the art.

Composite

A composite is a combination of two materials of different natures. In the present invention, this is a combination of particles stemming from a metal powder in a set organic or inorganic matrix, formed by the "binder"/"binding agent".

Binding Agent

A binding agent according to the present invention relates to a product which binds the molecules of an element with another element, during the melting (generally cold melting) of materials. For example, in the present scenario, a binding agent will promote agglomeration of the particles of powder in a set matrix which may be polymeric.

Setting Catalyst

The setting catalyst allows acceleration, or even feasibility of the polymerization in a matrix which may be hard or flexible. The catalyst may be replaced by a heat treatment. The polymer is often prepared by cross-linking of two ingredients, one of which is typically a "resin", reacting under the action of heat in the presence of reagents (catalyst and polymerization accelerator). The three-dimensional structure (lattice) formed, stable, typically has a thermomechanical and chemical resistance.

Kevlar®

Kevlar® is a poly(p-phenyleneterephthalamide) (PPD-T), a thermoplastic polymer, consisting of aromatic rings separated by amide groups. This material is very well known by one skilled in the art who will use the type of adequate Kevlar® for obtaining the intended hardness of the external envelope.

Room Temperature

Room temperature is the one generally admitted as comprised between 15 and 30° C., preferentially between 20 and 25° C.

External Envelope

An external envelope according to the present invention may be placed at any location of the relevant vessel where it may then fulfill its technical function, for example biocidal (anti-fouling), reduction in the friction of the outer liquid with the immersed elements, or pigment elements.

Thus the external envelope according to the present invention may have a various thickness of a few microns to several centimeters. The thickness of the external envelope is advantageously comprised between 10 µm to 30 cm, more advantageously between 50 µm and 15 cm, even more advantageously between 100 µm and 5 cm, further more advantageously between 150 µm and 1 cm such as 200 µm, or further between 500 µm and 1 mm. The external envelope may have a substantially constant thickness.

Molding

The molding technique consists of taking an imprint which will then be used as a mold. Thus a molding may be used within the scope of the present invention for molding the different objects comprising an external envelope according to the present invention.

According to the present invention, the molding therefore consists of placing a composite in a mold of which it will take the shape and then of removing it therefrom. The composites according to the present invention may thereby be used for molding these objects. The object which ensues from this molding may be hollow or filled with the composite or another material, such as a polymer without any metal powder for example.

Anti-fouling

An anti-fouling within the scope of the present invention is an anti-dirt surface containing biocides intended to prevent aquatic organisms from binding to the hull of ships or on other immersed objects.

Biocide

The definition of the term of "biocide" according to the present invention joins up with that of the European Parliament and European Council Directive no. 98/8/CE as of Feb. 16, 1998 relating to the marketing of biocidal products (JOCE No. L 123 as of Apr. 24, 1998) which define them as being "Active substances and preparations containing one or several active substances which are presented in the form in which they are delivered to the user, which are intended for destroying, pushing back or making inoffensive the harmful organisms, of preventing the action thereof or combatting them in any other way, by a chemical or biological action".

Bio-corrosion

The term of "bio-corrosion" according to the present invention relates to the corrosion of materials directly due or subsequent to the action of live organisms. These live organisms may be microscopic or macroscopic, unicellular or multicellular, such as bacteria, algae, fungi, shellfish, etc.

Pigment

Within the scope of the present invention, by "pigment" is understood a coloring substance insoluble in the matrix of the material which contains it. Preferentially, the pigment is a coloring substance of a composite, i.e. for dying in the bulk a composite comprising a binding agent and optionally a setting catalyst. Preferably, the pigments according to the present invention give the possibility of obtaining coatings/ composites of black colors, anthracites color, or black color with slight brown reflections, or further dark brown according to the nature and the concentration of the pigment (powder), in particular by the use of powders of oxidized metals, like oxidized copper.

DETAILED DESCRIPTION

A factor which should be taken into account within the scope of the present invention is the grain size of the powder. Indeed, the grain size of the metal powder according to the present invention will be determining in order to produce the external envelope. Indeed, if the powder is too fine, unlike what could be expected before the carrying out of the present invention, the composite used for making the external envelope does not form properly and has unacceptable physico-chemical properties (hardness, friability, flexibility, etc.). Thus, it seems that there is a threshold which is located towards 30% by mass of powder grains relatively to the total amount of powder, the diameter of which should be greater than 45 μm so that the final composite coating may be made.

The determination of the grain size of the powder may be achieved by any adequate method, in particular the one described by the ISO4497 standard or adapted from the latter. This international standard specifies a method for determining the grain size distribution of metal powders by sifting under dry conditions in grain size fractions.

Thus, the metal powder may contain more than 40%, 50%, 75%, 90%, 95%, 100% by mass of grains for which the diameter is greater than 45 μm.

Further, it seems important in certain embodiments of the present invention that at least one proportion, even very small, of the powder has a diameter of less than 45 μm. Thus, in a particular embodiment, the metal powder, preferentially of oxidized copper and/or containing phosphorus, does not contain more than 70%, 50%, 25%, 10%, 5%, 2% or 1% by mass of grains for which the diameter is less than 45 μm.

These particular embodiments wherein the maximum amount of grains for which the diameter is less than 45 μm are defined, may be individually combined to ranges of a minimum amount of grains for which the diameter is less than 63 μm at most in the composition of metal powder, preferentially of oxidized copper and/or phosphorus-containing, according to the present invention. Thus, the metal powder contains at least 1%, 5%, 10%, 25%, 50%, 75%, 90% or 95% by mass of grains for which the diameter is less than 63 μm.

In an embodiment of the present invention, the powder grains are all less in diameter than 500 μm. Advantageously, the powder grains are all less in diameter than 250 μm, 200 μm, 150 μm, 100 μm, 90 μm, 80 μm, 70 μm or 60 μm.

Thus, more particularly, the object of the present invention relates to a metal powder composition, preferentially of oxidized copper and/or containing phosphorus, as defined above wherein the grain size has specific characteristics which are detailed below.

According to a particular embodiment of the invention, the powder contains grains with the following diameters D:
  1±1% by mass of grains of diameter D1: 125 μm≤D1
  2±2% by mass of grains of diameter D2: 106 μm≤D2<125 μm
  12±10% by mass of grains of diameter D3: 75 μm≤D3<106 μm
  10±5% by mass of grains of diameter D5: 63 μm≤D5<75 μm
  20±10% by mass of grains of diameter D6: 45 μm≤D6<63 μm
  40±30% by mass of grains of diameter D7: D7≤45 μm According to an advantageous embodiment of the invention, the powder contains grains with the following diameters D:
  1±1% by mass of grains of diameter D1: 125 μm≤D1
  2±2% by mass of grains of diameter D2: 106 μm≤D2<125 μm
  5±5% by mass of grains of diameter D3: 90 μm≤D3<106 μm
  7±5% by mass of grains of diameter D4: 75 μm≤D4<90 μm
  10±5% by mass of grains of diameter D5: 63 μm≤D5<75 μm
  20±10% by mass of grains of diameter D6: 45 μm≤D6<63 μm
  40±30% by mass of grains of diameter D7: D7≤45 μm According to an advantageous embodiment of the invention, the powder contains grains with the following diameters D:
  1±0.5% by mass of grains of diameter D1: 125 μm≤D1
  2±1% by mass of grains of diameter D2: 106 μm≤D2<125 μm
  5±2% by mass of grains of diameter D3: 90 μm≤D3<106 μm
  7±2% by mass of grains of diameter D4: 75 μm≤D4<90 μm
  10±3% by mass of grains of diameter D5: 63 μm≤D5<75 μm
  20±5% by mass of grains of diameter D6: 45 μm≤D6<63 μm
  50±20% by mass of grains of diameter D7: D7≤45 μm According to a more advantageous embodiment of the invention, the powder contains grains of the following diameters D:
  09±0.1% by mass of grains of diameter D1: 125 μm≤D1
  1.5±0.5% by mass of grains of diameter D2: 106 μm≤D2<125 μm
  4.5±1% by mass of grains of diameter D3: 90 μm≤D3<106 μm
  6.5±1% by mass of grains of diameter D4: 75 μm≤D4<90 μm
  8.5±1% by mass of grains of diameter D5: 63 μm≤D5<75 μm
  18±5% by mass of grains of diameter D6: 45 μm≤D6<63 μm
  60±10% by mass of grains of diameter D7: D7≤45 μm According to a more advantageous embodiment of the invention, the powder contains grains with the following diameters D:
  0.9±0.1% by mass of grains of diameter D1: 125 μm≤D1
  1.5±0.5% by mass of grains of diameter D2: 106 μm≤D2<125 μm
  4.5±1% by mass of grains of diameter D3: 90 μm≤D3<106 μm
  6.5±1% by mass of grains of diameter D4: 75 μm≤D4<90 μm
  8.5±1% by mass of grains of diameter D5: 63 μm≤D5<75 μm
  18±5% by mass of grains of diameter D6: 45 μm≤D6<63 μm
  60±5% by mass of grains of diameter D7: D7≤45 μm According to an even more advantageous embodiment of the invention, the powder contains grains of the following diameters D:
  0.9% by mass of grains of diameter D1: 125 μm≤D1
  1.5% by mass of grains of diameter D2: 106 μm≤D2<125 μm 4.5% by mass of grains of diameter D3: 90 μm≤D3<106 μm 6.6% by mass of grains of diameter D4: 75 μm≤D4<90 μm 8.4% by mass of grains of diameter D5: 63 μm≤D5<75 μm 20.8% by mass of grains of diameter D6: 45 μm≤D6<63 μm 58.8% by mass of grains of diameter D7: D7≤45 μm According to an advantageous embodiment of the invention, the powder contains grains of the following diameters D:

1.0% by mass of grains of diameter D2: 106 μm≤D2

8.1% by mass of grains of diameter D3': 75 μm≤D3'<106 μm 7.9% by mass of grains of diameter D5: 63 μm≤D5<75 μm 19.2% by mass of grains of diameter D6: 45 μm≤D6<63 μm 63.8% by mass of grains of diameter D7: D7≤45 μm Conventionally, the mass percentages are added so as to have a cumulative grain size according to the ISO 4497 standard. It is easy for one skilled in the art considering the ranges given above to simply add the values for again finding the present standards of the grain size (cumulative).

As stated previously, these values of grain size are independent of the chemical nature of the powder, and simply give the possibility of incorporating the powders in a binder. However, variations of particular technical effects (biocidal nature, flow rate, pigmentation) may be obtained according to the fineness of the powder.

More particularly, the object of the present invention relates to a vessel hull as described presently, characterized in that the metal powder is a powder comprising at least one metal selected from among magnesium, tin, technetium, rhenium, titanium, iron, chromium, cobalt, gold, zinc, platinum, cadmium, aluminium, nickel, silver, beryllium, calcium, strontium, copper, preferentially aluminium and/or copper.

The invention therefore also relates to a vessel hull comprising in an external envelope intended to be in contact with an outer liquid element, a metal powder characterized in that:

said powder
contains more than 30% by mass of grains for which the diameter is greater than 45 μm and
is partly in contact with said outer liquid element;
the external envelope has a thickness of less than 0.2 mm, advantageously less than 0.3 mm, 0.5 mm, 0.6 mm, 0.7 mm, 0.8 mm, 0.9 mm or 1 mm In a particular embodiment, said external envelope comprises a concentration gradient of powder grains.

The present invention is thus directed towards the use of an external envelope of a vessel hull as defined above for reducing the consumption and/or a gain in speed of the relevant vessel.

As regards the density of the powders used, generally the latter is comprised between 1 and 5 g/cm$^3$, more particularly between 1.5 and 3 g/cm$^3$, between 1.5 and 2 g/cm$^3$, between 2 and 3 g/cm$^3$, between 2 and 2.5 g/cm$^3$, between 2.5 and 3 g/cm$^3$. The density will depend both on the grain size and on the chemical nature of the powder, for example on its oxidation degree.

Thus, the object of the present invention relates to a vessel hull such as described presently, characterized in that the external envelope comprises a concentration gradient of powder grains, for example oriented from the inside to the outside of the vessel and preferentially increasing.

The object of the present invention thus relates to a vessel hull as characterized above in that the copper is phosphorus-containing or oxidized, preferentially with an oxidation level of the copper greater than 95% by mass of oxidized copper with respect to the total mass of copper in the powder. In the case of phosphorus-containing copper, the mass phosphorus amount may be comprised between 0 and 8%, more particularly between 2 and 7%.

More particularly, the object of the present invention comprises a composition of metallic copper powder (Cu$^0$), of oxidized copper and/or phosphorus-containing copper as defined above wherein the copper mass is greater than or equal to 65%, advantageously greater than 70%, more advantageously greater than 75%, further more advantageously greater than 80%, even more advantageously greater than 85%, even more advantageously greater than 90%, even more advantageously greater than 95%, even more advantageously greater than 97%, even more advantageously greater than 98%, even more advantageously greater than 99%, even more advantageously greater than 99.5%, even more advantageously greater than 99.9% by mass as compared with the total mass of the powder composition. The oxidized copper composition according to the present invention is characterized in that the copper is oxidized at various degrees, i.e. ranging from a surface oxidation of the copper grains to a core oxidation.

Preferentially, the oxidized copper composition according to the present invention is characterized in that the copper grains are oxidized to the core.

The oxidized copper composition according to the present invention is characterized in that the copper is oxidized at various levels, for example, the oxidized copper composition may be oxidized to 5%, 10%, 15%, 20%, 25%, 30%, 35%, 40%, 45%, 50%, 55%, 60%, 65%, 70%, 75%, 80%, 85%, 90% or 95% by mass of oxidized copper with respect to the total mass of copper.

This oxidation degree gives the possibility of adjusting the biocidal activity of the outer envelope of the vessel.

According to an embodiment of the present invention, the oxidized copper composition incorporated into the external envelope according to the present invention is characterized in that the oxidation level of the copper is greater than 95% by mass of oxidized copper based on the total mass of copper and/or that the amount of phosphorus is comprised between 2 and 16%, preferentially 8% by mass based on the total mass of the powder.

For example, according to an embodiment of the present invention, the oxidized copper composition incorporated into the external envelope according to the present invention is characterized in that the oxidation level of the copper is 95.5%, 96%, 96.5%, 97%, 97.5%, 98%, 98.5%, 99%, 99.5%, 99.7%, 99.8%, 99.9% or 100% by mass of oxidized copper based on the total mass of copper.

Further, the techniques for determining the copper level are extremely common in the art and may be accomplished by chemical and/or physical routes.

The object of the present invention further relates to a vessel hull as characterized above in that the metal powder comprises at least one non-metal inorganic compound such as nitrogen, oxygen, phosphorus, arsenic, sulfur, fluorine, chlorine, bromine, carbon, silicon.

The object of the present invention also relates to a vessel hull as above, characterized in that said metal powder is comprised in an organic or inorganic binder, or a mixture of both, thereby forming a composite.

The object of the present invention further relates to a vessel hull as above, characterized in that the organic binder is an organic polymer preferentially selected from among polyester, polyurethane, epoxy polymer, vinyl ester or in that the inorganic binder is an inorganic polymer preferentially selected from among silica, polydimethylsiloxanes, polythiazyls, polysilanes, polygermanes, more preferentially a silica polymer.

The object of the present invention further relates to a vessel hull as above, characterized in that the composite comprises a mass proportion of powder/binder comprised from 1/2 to 2/1 respectively, preferentially from 1.25/1 to 1.6/1 respectively. For example the composite of metal powder and of the binding agent as defined above is characterized in that the mass proportion of the powder composition/binder is comprised from 1.1/1 to 1.8/1 respectively, from 1.15/1 to 1.6/1 respectively, from 1.2/1 to 1.4/1 respectively, from 1.25/1 to 1.3/1 respectively, or is 1.275/1 respectively.

The object of the present invention also relates to a vessel as above, characterized in that the composite comprises fiber materials, such as glass fiber, carbon fiber, Kevlar®, or a mixture thereof.

The object of the present invention further relates to a vessel hull such as described presently, characterized in that it is selected from among a boat, a sub-marine, a wind surfing board, a kite surf, a water ski, a wake board, a surf, a paddle board, a jet ski, a canoe or a kayak.

The object of the present invention also relates to a manufacturing method as described above.

The making of a metal powder as defined above is accomplished by usual techniques in the field. Generally, the fractionation of the powder metal may be accomplished by any technique known in the art, whether this is by mechanical, chemical, physical fractionation, etc. It is possible to obtain the desired powder according to the present invention directly by an adequate fractionation, which implies a perfect control of the technique by the operator who nevertheless resorts to the common knowledge in the art. An alternative technique which is more easy is further well known in the art, which consists of fractionating the material in a coarse way and not very regular in grain size, and then by the operation of successive siftings, for isolating populations of particular powders (i.e. having particular and regular grain sizes). Within the scope of the present invention, this technique is quite applicable: A coarse fractionation may be performed, followed by a sampling and isolating step of the particular powders, and then by a step for selecting powders in order to reform the powder according to the invention. These techniques are extremely common in the art. The control of the grain size is actually part of the general knowledge of one skilled in the art. Thus, it is obvious that in the context of the present invention the possibility of adding other compounds/powders in order to obtain a "mixed" composition, having the technical effects described presently in addition to other effects provided by the compounds/secondary powders added. Advantageously, the powders with the determined grain sizes were obtained by any of the fractionation techniques known in the art, followed by at least two passages over molecular sieves giving the possibility of ensuring that the size of the particles making up the powder are neither too small or too large in determined amounts, thereby ensuring perfect control of the essential characteristics required for carrying out the present invention. Nevertheless and preferentially, the fractionation is accomplished with an atomization technique, for example with water (subsequently to metal fusion).

Thus, the method for manufacturing a composition according to the present invention is characterized in that the metal powder, preferentially oxidized metal copper ($Cu^0$, and/or phosphorus-containing) copper is directly obtained by fractionation or is reformed from several powders to the determined grain sizes and metal (e.g. copper) proportions.

Advantageously, the particles obtained with such techniques are comprised between 8 and 150 μm (D50) and/or the amount of oxygen comprised in the composition is between 0.3 and 5% by weight.

Nevertheless, according to an embodiment of the invention the oxidization of the copper strictly speaking may be accomplished after the fractionation by passing the composition into the oven under a controlled atmosphere.

For example, as regards the oxidized copper powder, the oxidization may be accomplished at a temperature equal to or greater than 500° C., in the presence of oxygen and/or of an oxygen source, preferentially in the presence of magnesium or of phosphorus. According to an embodiment, the temperature is greater than 800° C., 1,000° C., 1,500° C. or 2,000° C.

It may be directly blown onto the copper, oxygen or a gas containing oxygen. Generally this is accomplished in free air. A compound may also be incorporated into the powder which, when it is heated, will release oxygen. Of course, the copper may be fractionated before being heated for allowing a better oxidation. The copper may nevertheless be oxidized before its fractionation as a powder.

Thus, the object of the present invention relates to a method for manufacturing a vessel hull as described above, characterized in that the metal powder is mixed with the binder before the deposition step a.

The object of the present invention also relates to a method for manufacturing a vessel hull as described above, characterized in that the metal powder comprises at least one metal selected from among magnesium, tin, technetium, rhenium, titanium, iron, chromium, cobalt, gold, zinc, platinum, cadmium, aluminium, nickel, silver, beryllium, calcium, strontium, copper, preferentially aluminium and/or copper.

The object of the present invention further relates to a method for manufacturing a vessel hull as described above, characterized in that the powder contains at least 60% by mass of copper.

Further, the object of the present invention relates to a method for manufacturing a vessel hull as described above characterized in that the copper is oxidized or phosphorus-containing.

The object of the present invention relates to a method for manufacturing a vessel hull as described above, characterized in that the oxidation level of the copper is greater than 95% by mass of oxidized copper based on the total mass of copper.

The object of the present invention relates to a method for manufacturing a vessel hull as described above, characterized in that the metal powder comprises at least one non-metal inorganic compound such as nitrogen, oxygen, arsenic, sulfur, fluorine, chlorine, bromine, carbon, silicon.

The object of the present invention relates to a method for manufacturing a vessel hull as described above, characterized in that the binder is an organic polymer, preferentially selected from among polyester, polyurethane, an epoxy polymer, a vinyl ester or in that the binder is an inorganic polymer preferentially selected from among silica, polydimethylsiloxanes, polythiazyls, polysilanes, polygermanes, more preferentially a silica polymer.

The object of the present invention relates to a method for manufacturing a vessel hull as described above, characterized in that the mass proportion of metal powder/binder is comprised from 1/2 to 2/1 respectively, preferentially from 1.25/1 to 1.6/1 respectively. For example, the composite of metal powder and of the binding agent as defined above is characterized in that the mass proportion by of the powder composition/binder is comprised from 1.1/1 to 1.8/1 respectively, from 1.15/1 to 1.6/1 respectively, from 1.2/1 to 1.4/1 respectively, from 1.25/1 to 1.3/1 respectively, or is 1.275/1 respectively.

The object of the present invention relates to a method for manufacturing a vessel hull as described above, characterized in that the composite comprises fiber materials, such as glass fiber, carbon fiber, Kevlar®, or a mixture thereof.

FIGURES

FIG. 1: Photograph of a boat hull made according to the present invention.

The hull (in contact with the water) is in a composite according to the present invention, the upper portion of the hull (white in the photograph) is in a more common composite.

EXAMPLES

In order to illustrate the present invention, the following examples were made. By no means is the object of the present invention limited to these single examples.

1. A $CuP_8$-based Powder

The powder of $CuP_8$, for which the grain size is not controlled is known for being used in brazing.

Conventionally, the latter has the following characteristics:
  Rated composition (mass %): Cu: 92
    P: 8
  Melting point: 710-750° C.
  Density: 8 g/cm³
  Procedure for making the copper-phosphorus powder according to the invention. According to the present invention, the copper-phosphorus alloy containing a phosphorus percentage between 2 and 16%, preferably 8%, is introduced into the melting bath. This alloy is then atomized with water under conditions such that the grain size result has to be found between 8 and 150 µm (D50), the oxygen level is comprised between 0.3 and 5% by weight.

The following powder was thereby obtained:

TABLE 1

| Grain size, retained accumulated % (ISO4497) | | |
| --- | --- | --- |
| Particle sizes | Percentage per slice | Retained accumulated percentages |
| ≥125 µm | 0.0 | 0.0 |
| ≥106 µm | 0.9 | 0.9 |
| ≥90 µm | 4.5 | 5.4 |
| ≥75 µm | 6.6 | 12.0 |
| ≥63 µm | 8.4 | 20.4 |
| ≥45 µm | 20.8 | 41.2 |
| <45 µm | 58.8 | 58.8 |
| Total | 100% | 100% (41.2 + 58.8) |

Obtained density: 2.67 g/cm³ (ISO3923/2)
Obtained P %: 8.0% by mass

2. Oxidized Copper Powder

The same procedure as for the copper-phosphate was applied for the copper. The following powder was thereby obtained:

TABLE 2

| Grain size, retained accumulated % (ISO4497) | | |
| --- | --- | --- |
| Particle sizes | Percentages per slice | Retained accumulated percentages |
| ≥125 µm | 0.0 | 0.0 |
| ≥106 µm | 1.0 | 1.0 |
| ≥75 µm | 8.1 | 9.1 |
| ≥63 µm | 7.9 | 17.0 |
| ≥45 µm | 19.2 | 36.2 |
| <45 µm | 63.8 | 63.8 |
| Total | 100% | 100% (36.2 + 63.8) |

Obtained density: 2.88 g/cm³

$O_T$ %: 0.35% by mass (ISO4491-4)

Next, the obtained powder was passed into a strip oven at a temperature greater than 500° C. (about 800° C. in this case) for oxidizing it, under a controlled atmosphere.

A powder with the same grain size as earlier was obtained with:

Obtained density: 1.60 g/cm³

$O_T$ %: 0.08% by mass

Cu %>99.7% by mass

3. Example of Obtained Composite/Coatings

The composites are simply obtained by mixing the compounds with each other.

Before proceeding with the manufacturing of the vessel hulls (expensive), tests were conducted by means of the coatings of the composites according to the present invention. The laying of the coatings of table 3 is accomplished in the following standard way.

First it is preceded with sanding or sand blasting of the surface to be treated (grain of 120).

The times for hardening the polyester primer (about 6 h at 20° C. per layer) were observed. It may then be preceded with active drying of the part with compressed air or by ovening at 25° C. in a cabin for 20 minutes. It is possible to degrease the surface to be treated.

It is quite possible to apply the composite with a roller or a gun (with in this case the requirement of observing a constant angle for projecting the composite on the surface at 90° for a maximum covering).

The storage of the coated product may be accomplished in a room treated in a controlled atmosphere at 20° C. ideally for 12 hours for efficient hardening (For a boat, this is more difficulty to obtain, this is why accelerated hardeners give the possibility of achieving the catalysis as far as a minimum of 5° C.). Once this hardening period is completed, sanding or sand blasting with a grain of 120 is carried out for getting rid from the surface of starch excesses and of oxide excesses and obtaining a smooth surface of metal.

TABLE 3

| | Composite 1 | Composite 2 | Composite 3 | Composite 4 |
|---|---|---|---|---|
| Metal powder | $CuP_8$ (powder of example 1) | Oxidized copper (powder of example 2) | Oxidized copper (powder of example 2) | $CuP_8$ (powder of example 1) |
| Binder (mass proportions) | Hybrid polyester 84% Acetone 8% Paraffin Styrene 2% Coloring agent 4% | Hybrid polyester 84% Acetone 8% Paraffin Styrene 2% Coloring agent 4% | Vinyl ester, ready for use commercially available | Vinyl ester, ready for use available commercially |
| Hardener (mass proportions) | METHYL ETHYL PEROXIDE, 2% | METHYL ETHYL PEROXIDE, 2% | | |
| Mass proportions of Powder/Binder | Powder = 1.275 Binder = 1 | Powder = 1.275 Binder = 1 | Powder = 1 Binder = 1.5 (estimated value) | Powder = 1 Binder = 1.5 (estimated value) |
| Achievable suspension | Yes | Yes | Yes | Yes |
| Setting time | 60 minutes | 60 minutes | 60 minutes | 60 minutes |

4. Examples of Biocidal Activities and Improvement of the Movement of Fluids

Results of the laboratory tests have shown that the coatings using the same type of composite as the present invention have remarkable biocidal properties (see examples of FR1357099, FR1400766, and PCT/EP2014 065 498).

Further, preliminary tests have shown that coatings using the same type of composite as the present invention have high biocidal properties (including anti-microbial properties) when they are exposed to various fluids such as water.

Further, laboratory tests have shown an increase in the rate of flow of fluid over the whole surface covered with coatings using the same composite as the present invention. Indeed, an ordinary plastic substrate was in one case, coated with the coating according to the invention (compound No. 2 in table 3—oxidized copper at 99.9%) and only in the other case with the composite binder of No. 2. A drop of liquid is deposited on each substrate at the same level and both coated substrates were tilted with the same angle relatively to the horizontal (as far as more or less 65°), which gave the possibility of directly comparing the rates of the descending liquid drops. This direct comparison gave the possibility of establishing that the coating using the same composite of the present invention gave the possibility of increasing the rate from 10 to 30% relatively to the binder alone. This inherent property of the coatings using the same composite of the present invention (which seems to be related to the presence of copper powder) gives the possibility of contemplating a long lasting way and without any cost of saving the energy expenditures as to the propulsion of vessels, or by increasing the speed thereof.

5. Boat Hull

A boat hull (cf. FIG. 1) was thereby produced. The composite used was that of formula No. 4 according to the table 3 above. The composite in the liquid state obtained was handled like any resin conventionally used for the manufacturing of such hulls of boats (and according to the general method described above). All the technical effects reckoned with of the thereby produced hull were obtained.

The invention claimed is:

1. A vessel hull comprising in an external envelope intended to be in contact with an outer liquid element, a metal powder wherein:
    said powder
        contains more than 30% by mass of grains for which the diameter is greater than 45 μm and
        is partly in contact with said outer liquid element;
    wherein the envelope has a thickness of less than 1 mm, and wherein the powder comprises a copper powder with at least 60% by mass of copper based on the mass of powder.

2. The vessel hull according to claim 1, wherein the metal powder comprises at least one metal selected from the group consisting of magnesium, tin, technetium, rhenium, titanium, iron, chromium, cobalt, gold, zinc, platinum, cadmium, aluminium, nickel, silver, beryllium, calcium, strontium, and copper.

3. The vessel hull according to claim 1, wherein the external envelope comprises a concentration gradient of powder grains oriented in the thickness direction of the external envelop, and wherein the gradient is more concentrated near the vessel surface.

4. The vessel hull according to claim 1, characterized in that the copper is phosphorus-containing or oxidized with an oxidation level of the copper greater than 95% by mass of oxidized copper with respect to the total mass of copper in the powder.

5. The vessel hull according to claim 1, wherein the metal powder comprises at least one non-metal inorganic compound selected from the group consisting of nitrogen, oxygen, phosphorus, arsenic, sulfur, fluorine, chlorine, bromine, carbon, and silicon.

6. The vessel hull according to claim 1, wherein said metal powder is comprised in an organic or inorganic binder, or a mixture of both, thereby forming a composite.

7. The vessel hull according to claim 6, wherein the organic binder is an organic polymer selected from the group consisting of polyester, polyurethane, epoxy polymer, and vinyl ester or wherein the inorganic binder is an inorganic polymer selected from the group consisting of silica polymer, polydimethylsiloxanes, polythiazyls, polysilanes, and polygermanes.

8. The vessel hull according to claim 6, wherein the composite comprises a mass proportion of powder/binder comprised from 1/2 to 2/1 respectively.

9. The vessel hull according to claim 6, wherein the composite comprises fiber materials.

10. A hull, a foil, a directional element such as a rudder or a fin, a propulsion element such as a propeller or a jet pipe comprising an external envelope as defined according to claim 1.

11. A vessel comprising an external envelope as defined according to claim 1, wherein the vessel is selected from the group consisting of a boat, a submarine, a wind surfing board, a kite surf, a water ski, a wake board, a surf, a paddle board, a jet ski, a canoe and a kayak.

12. A method for manufacturing a vessel hull as defined according to claim 1, comprising the following steps:

a. providing a binder/metal powder mixture;
b. depositing a layer of the mixture on a mold of a vessel hull;
c. optionally adding fiber materials in said binder;
d. hardening the binder/metal powder mixture;
e. optionally adding at least one additional structure layer and/or reinforcement layer on the first hardened layer in step c; and
f. removing the vessel hull from the mold;

wherein the metal powder contains more than 30% by mass of grains for which the diameter is greater than 45 μm.

13. The manufacturing method according to claim 12, wherein the metal powder comprises at least one metal selected from the group consisting of magnesium, tin, technetium, rhenium, titanium, iron, chromium, cobalt, gold, zinc, platinum, cadmium, aluminium, nickel, silver, beryllium, calcium, strontium, and copper.

14. The manufacturing method according to claim 12, wherein the powder contains at least 60% by mass of copper.

15. The manufacturing method according to claim 13, wherein the metal powder comprises copper that is oxidized or phosphorus-containing.

16. The manufacturing method according to claim 15, wherein the oxidation level of the copper is greater than 95% by mass of oxidized copper based on the total mass of copper.

17. The manufacturing method according to claim 12, wherein the metal powder comprises at least one non-metal inorganic compound selected from the group consisting of nitrogen, oxygen, arsenic, sulfur, fluorine, chlorine, bromine, carbon, and silicon.

18. The manufacturing method according to claim 12, wherein the binder is an organic polymer selected from the group consisting of polyester, polyurethane, an epoxy polymer, a vinyl ester or wherein the binder is an inorganic polymer selected from the group consisting of silica polymer, polydimethylsiloxanes, polythiazyls, polysilanes, and polygermanes.

19. The manufacturing method according to claim 12, wherein the mass proportion of metal powder/binder is comprised from 1/2 to 2/1 respectively.

20. The manufacturing method according to claim 12, wherein the composite comprises fiber materials.

* * * * *